United States Patent [19]  
Kittelsen

[11] Patent Number: 5,460,527  
[45] Date of Patent: Oct. 24, 1995

[54] COMPOSITE DENTAL BLEACHING TRAY

[75] Inventor: Jon D. Kittelsen, Fridley, Minn.

[73] Assignee: E-Z Gard Industries, Inc., Minneapolis, Minn.

[21] Appl. No.: 293,489

[22] Filed: Aug. 22, 1994

Related U.S. Application Data

[63] Continuation-in-part of Ser. No. 66,469, May 24, 1993, Pat. No. 5,339,832, and Ser. No. 127,759, Sep. 28, 1993, Pat. No. 5,385,155.

[51] Int. Cl.⁶ ..................................................... A61C 5/14
[52] U.S. Cl. .......................... 433/215; 128/862; 128/859
[58] Field of Search .................................. 128/862–859, 128/857, 848; 601/139; 433/6, 37, 42, 43, 215

[56] References Cited

U.S. PATENT DOCUMENTS

| | | |
|---|---|---|
| 257,038 | 4/1882 | McMann . |
| D. 328,494 | 8/1992 | Schwendeman et al. ............. D24/176 |
| 1,117,928 | 11/1914 | Thurmond . |
| 1,323,832 | 12/1919 | Chige . |
| 1,461,209 | 7/1923 | Bridges . |
| 1,470,888 | 10/1923 | Smedley . |
| 1,487,392 | 3/1924 | Lee . |
| 2,118,980 | 5/1938 | Montgomery et al. ..................... 32/17 |
| 2,257,709 | 9/1941 | Anderson .................. 601/339 |
| 3,073,300 | 1/1963 | Berghash ................. 128/862 |
| 3,319,626 | 5/1967 | Lindsay ................. 128/861 |
| 4,673,791 | 8/1988 | Halverson et al. ................. 206/570 |
| 5,031,638 | 7/1991 | Castaldi ................. 128/862 |
| 5,076,785 | 12/1991 | Tsai ................. 433/46 |
| 5,082,007 | 1/1992 | Adell ................. 128/862 |
| 5,152,301 | 10/1992 | Kittelsen et al. ................. 128/861 |
| 5,165,424 | 11/1992 | Silverman ................. 128/861 |
| 5,277,203 | 1/1994 | Hays ................. 128/862 |
| 5,316,474 | 5/1994 | Robertson ................. 433/37 |
| 5,320,114 | 6/1994 | Kittelsen et al. ................. 128/861 |
| 5,336,086 | 8/1994 | Simmen et al. ................. 433/37 |

Primary Examiner—Robert A. Hafer  
Assistant Examiner—Michael O'Neill  
Attorney, Agent, or Firm—Palmatier, Sjoquist & Helget

[57] ABSTRACT

A composite bleaching tray has a U-shaped base composed of a nonsoftening, resilient, low compression elastomer. The U-shaped base has an upward outer labial wall. A flexible and tough, softenable thermoplastic sealing portion is molded to the top of the outer labial wall and forms an inner lingual wall. A handle is attached to the U-shaped base for immersing the tray in boiling water for softening the thermoplastic sealing portion. The handle is removable after the bleaching tray is fitted to the mouth. The bleaching tray also includes a sizing kit for selection of the correctly sized small to large bleaching tray for the user.

9 Claims, 3 Drawing Sheets

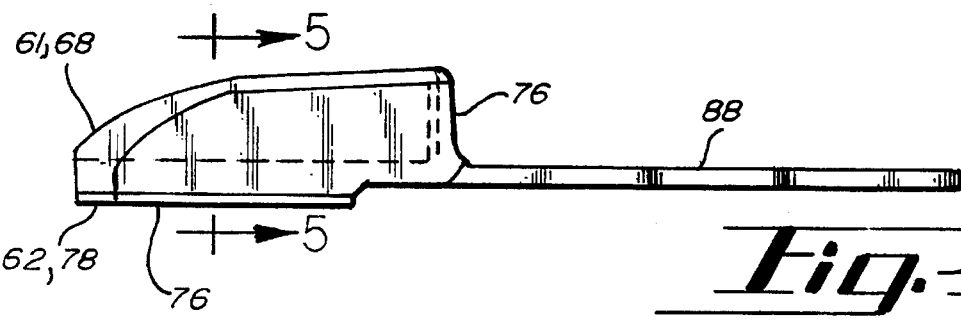
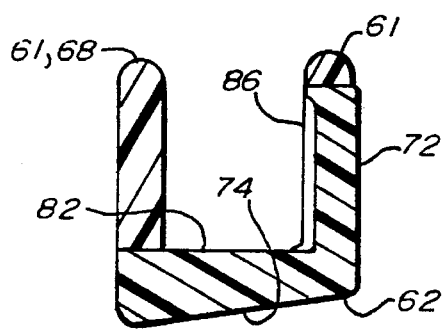
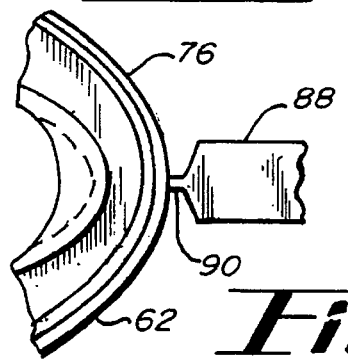
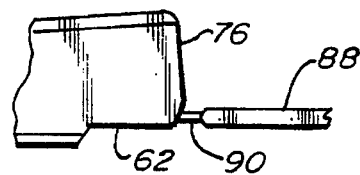
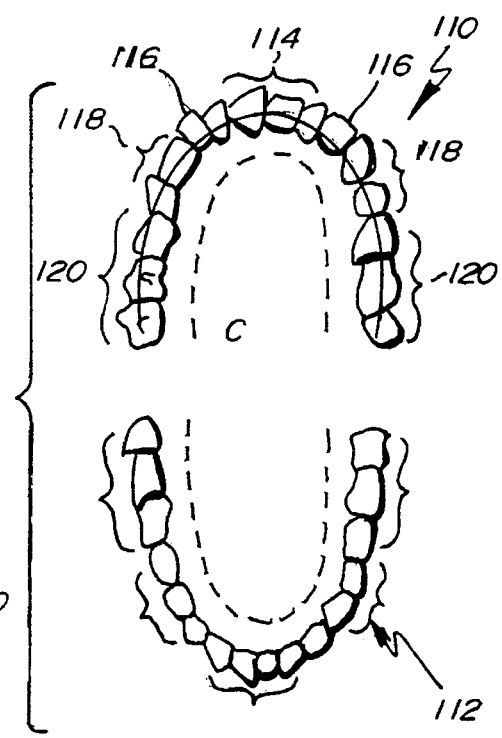
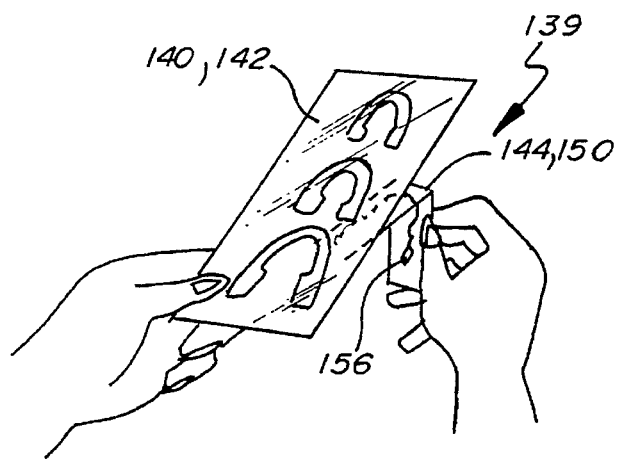

COMPOSITE DENTAL BLEACHING TRAY

This is a continuation-in-part of U.S. patent applications Ser. Nos. 08/066,469 and 08/127,759, which are U.S. Pat. Nos. 5,339,832 and 5,385,155 respectively.

BACKGROUND OF THE INVENTION

Bleaching trays are used by dental professionals to bleach a person's teeth. In the current art, creating a bleaching tray that fits an individual's mouth requires dental expertise and a substantial amount of labor.

First, a custom splint must be made. Splints are created by taking an impression of the upper and lower jaws. Thereafter, a positive model is made and the splint is vacuum formed over the positive model.

Then, the custom splint becomes a bleaching tray which is filled with bleaching gel and inserted into the mouth around the teeth of the upper and lower jaw. The wearer then bites down on the bleaching tray and holds the tray in place within the mouth for several hours, during which the bleaching gel bleaches the teeth.

Problems with bleaching trays of the current art are well known. Not only is the process of forming the bleaching tray labor intensive and requiring dental expertise, but the bleaching gel often comes out of the tray and the tray does not readily hold the gel as it lacks a cavity between the tray and the teeth. To overcome the latter problem, it is customary to coat the tooth impressions on the positive model with an enamel, such as fingernail polish, in order to create a slight pocket for the bleaching gel.

There is a need for a bleaching tray which is simple to fit without requiring the complicated steps of making splints and which has pockets for the bleaching gel. Additionally, the tray should be fittable by the wearer without dental expertise. Furthermore, the tray should be comfortable to wear for the several hours required to bleach the teeth and should not overly interfere with the wearer's breathing or speech. A sizing kit should be supplied with the tray for use by the inexperienced and health care professionals that will assist in fitting the tray. Such a kit should allow for correct tray sizing, to be simple and uncomplicated, safe and not reusable, easy to use and thereby permit the tray user to avoid trying various tray sizes.

SUMMARY OF THE INVENTION

A composite bleaching tray has a U-shaped base composed of a nonsoftening, resilient, low compression elastomer. The U-shaped base has an upward outer labial wall. A flexible and tough, softenable thermoplastic sealing portion is molded to the top of the outer labial wall and forms an inner lingual wall. A handle is attached to the U-shaped base for immersing the tray in boiling water for softening the thermoplastic sealing portion. The handle is removable after the bleaching tray is fitted to the mouth. The bleaching tray also includes a sizing kit for selection of the correctly sized small to large bleaching tray for the user.

A principal object and advantage of the present invention is that it provides a dental bleaching tray which can be fitted to the wearer without dental expertise.

Another object and advantage of the present invention is that eliminates much of the labor and expense involved in fitting a bleaching tray to the wearer's mouth.

Another object and advantage of the present invention is that it has bleaching gel pockets molded into the tray, reducing the possibility of the bleaching gel falling out of the tray.

Another object and advantage of the present invention is that it provides a U-shaped base composed of a nonsoftening, resilient, low compression, elastomer framework combined with a flexible and tough, softenable thermoplastic sealing portion which can be fitted to the wearer's mouth by immersion in boiling water. The tray essentially keeps its shape with bleaching gel pockets intact, while the thermoplastic sealing portion forms a tight seal to the wearer's gums.

Another object and advantage of the present invention is that it is comfortable to wear for the several hours needed to bleach the teeth, creating a breathing airway and facilitating speech.

Another object and advantage of the present invention is that it has a handle for dipping in boiling water which may be removed after the tray is fitted to the wearer's mouth, either by being cut off or by being broken away.

Another object and advantage of the present invention is that it provides a sizing kit for selection of the correctly sized small to large bleaching tray for the user.

Other objects and advantages will become obvious with a reading of the following specification and appended claims with a review of the figures.

BRIEF DESCRIPTION OF THE DRAWINGS

FIG. 4 is a side elevational view of the composite bleaching tray.

FIG. 5 is a cross-section taken along lines 5—5 of FIG. 4.

FIG. 6 is a top view of an alternative embodiment of the composite bleaching tray with an easily detachable handle.

FIG. 7 is a side elevational view of the alternative embodiment shown in FIG. 6.

FIG. 8 is a plan view of the upper and lower dentitions of the mouth.

FIG. 15 is a perspective view of the mouthguard sizing kit wherein the sizing strip with its dental imprint is being compared to the sizing chart for selection of the properly sized mouthguard.

DETAILED SPECIFICATION

Figure 1:
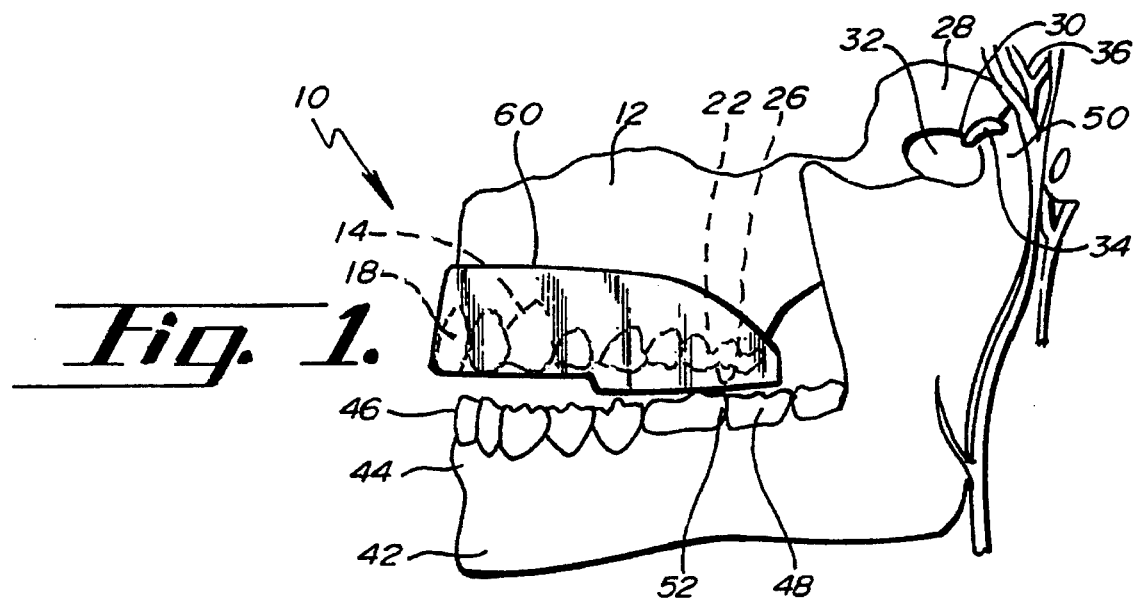
FIG. 1 is a maxillary mandibular buccal or partial side elevational view of the jaws and temporomandibular joint of a user of a bleaching tray of the present invention.
Figure 2:
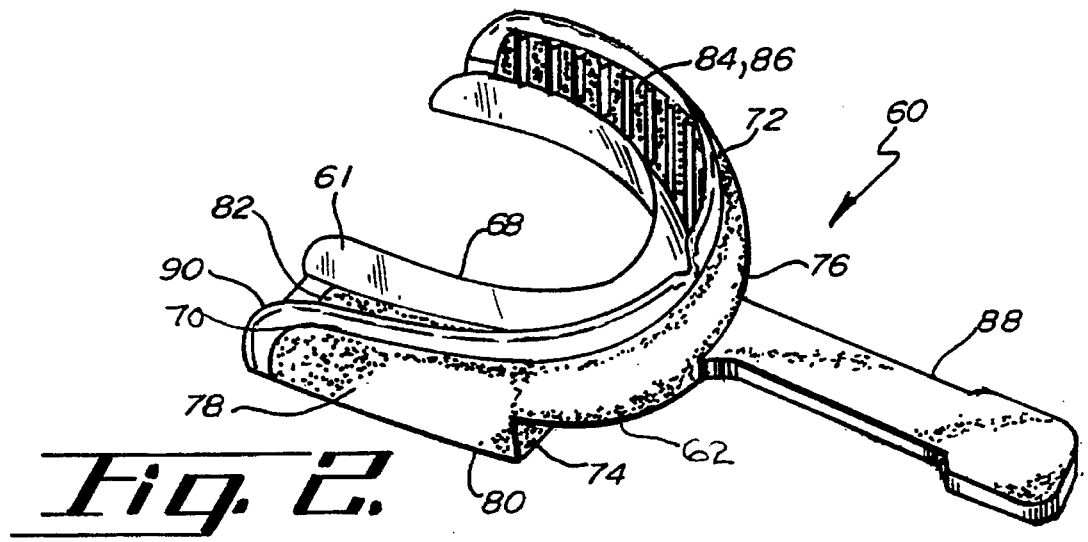
FIG. 2 is a perspective view of the composite bleaching tray.
Figure 3:
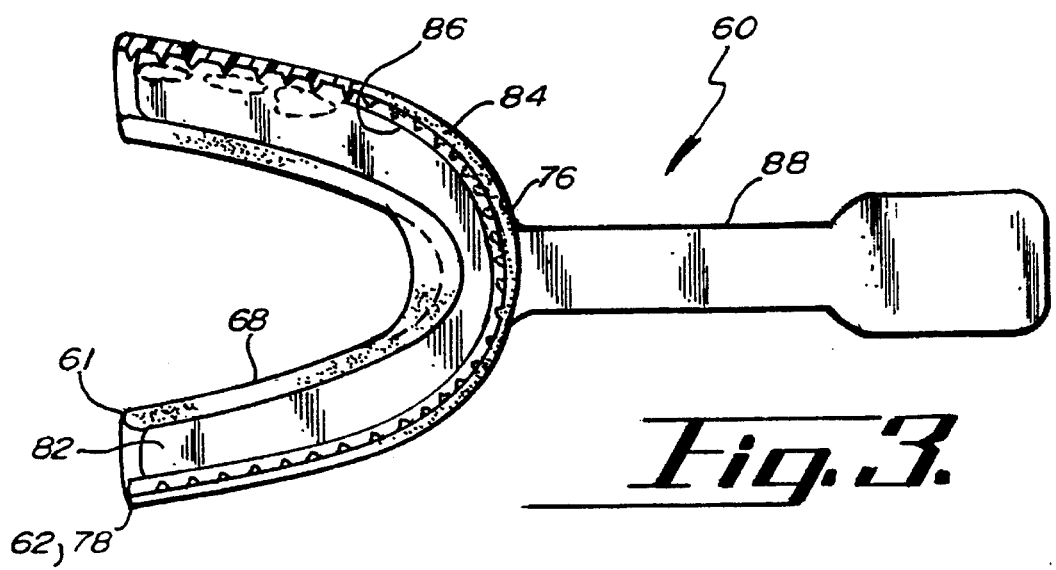
FIG. 3 is a top plan view of the composite bleaching tray.

To understand the structural features and benefits of the bleaching tray 60 of the present invention, some anatomy will first be described. Referring to FIG. 1, the bleaching tray user would have a mouth 10, generally comprised of a rigid upper jaw 12 and a movable lower jaw 42 which are movably connected at the temporomandibular joint (TMJ) 32 and 50.

More specifically, the rigid upper jaw 12 has gum tissue 14 within mouth 10. Gum tissue 14, as well as the bone thereunder, support anterior teeth (incisors and canines) 18 which have incisal or biting surfaces. The gum tissues 14 and the bone thereunder also support posterior teeth (molars and bicuspids) 22 which have cusps and biting surfaces 26.

Referring to one side of the human head, the temporal bone 28 is located upwardly and rearwardly of the upper jaw 12 and is in the range of 1/16 to 1/32 inch thick. The articular eminence 30 forms the beginning of the fossa 32 or the socket of the temporomandibular joint 32 and 50. Rearwardly and posteriorly to the articular eminence 30 is located cartilage 34. Through the temporomandibular joint 32 and 50 pass the auriculo-temporalis nerve 36 and the supra-temporal artery. Posteriorly to this structure is located the inner ear.

The movable jaw or mandible 42 supports a bone covered by gum tissue 44 which further supports anterior teeth (incisors and canines) 46 and posterior teeth (molars and bicuspids) 48 with occlusal surfaces 52. The condyle 50 of the lower jaw 42 forms the ball of the temporomandibular joint 32 and 50. This anatomical structure is the same for both sides of the head.

Referring to FIGS. 2–7, the composite bleaching tray may be generally seen. Bleaching tray 60 is comprised of a flexible and tough sealing portion 61 made of a second material, molded to a U-shaped base 62 made of a first material.

More particularly, the second material of the thermoplastic sealing portion 61 suitably may be made of copolymers of ethylene and vinyl acetate, such as ethylene vinyl acetate (EVA) which is commercially available and approved for oral use by the Food and Drug Administration. Extending upwardly from the U-shaped base 62 is inner lingual wall 68.

The U-shaped base 62 has an outer wall 72, bottom wall 74, anterior portion 76, and posterior portion 78. The thermoplastic sealing portion 61 is also molded to the top 70 of the U-shaped base 62.

The first material of the U-shaped base 62 suitably may be made of an elastomer, which unlike copolymers of ethylene and vinyl acetate, exhibits a high resilience, low compression, and shape maintenance. Virtually all rubbers that exhibit these physical characteristics may be utilized for the elastomer, including vulcanized rubber. Applicant has found a thermoplastic rubber marketed under the trademark KRATON® works well, which is marketed by GLS Plastics of 740B Industrial Drive, Cary, Ill. 60013. This thermoplastic rubber is unique in that it is injection moldable, FDA approved and readily adheres with copolymers of ethylene and vinyl acetate. Furthermore, the thermoplastic rubber has a melting or softening point significantly higher than that of EVA.

Consequently, the elastomer is initially molded or formed after which the thermoplastic sealing portion 61 may be injection molded therearound.

Located along the bottom wall 74 of the posterior portion 78 of the U-shaped base 62 are located posterior pads 80. These posterior pads 80 space apart the anterior teeth 46 of the lower jaw 42 from the anterior portion 76 of the bottom wall 74 of the U-shaped base 62. This arrangement forms a breathing airway and facilitates speech, thereby improving the comfort of the tray 60 as it is worn for several hours.

A channel 82 for receiving the teeth of the upper jaw is formed between the inner, lingual wall 68 of the sealing portion 61 and outer wall 72 and bottom wall 74 of the U-shaped base 62. The outer wall 72 of the U-shaped base 62 has a plurality of pockets 84 on its inner surface 86 facing the channel 82. The pockets 84 receive and hold bleaching gel for bleaching the teeth, thereby preventing the bleaching gel from falling out of the tray 60.

The tray 60 also has a handle 88 for immersing the tray 60 in boiling water. The handle 88 is connected to the anterior portion 76 of the U-shaped base 62. The handle 88 and U-shaped base 62 are preferably molded of a single piece of elastomer.

In operation, the composite bleaching tray 60 may be momentarily submersed suitably into boiling water by holding onto the handle 88. Thereafter, the bleaching tray 60 is immediately placed onto the teeth 18 and 22 of the upper jaw 12. The sealing portion 61 will have been softened by immersion in the boiling water, while the U-shaped base 62 will retain the correct shape of the tray, including the pockets 84 for bleaching gel. Next, the lower jaw 42 is positioned forwardly or anteriorly in a range of 1 to 4 millimeters as the posterior teeth 48 engage the occlusal posterior pads 80. The wearer or user then applies suction between the upper jaw 12 and the bleaching tray 60 while packing the bleaching tray 60 with the hands along the cheeks and lips adjacent the anterior and posterior teeth 18 and 22 of the upper jaw 12. The posterior teeth 48 of the lower jaw 42 will properly index upon the bottom surface of the occlusal posterior pads 76 or the posterior portion 78 of the U-shaped base 62.

After fitting the tray 60 to the mouth 10 the wearer, the tray 60 is removed from the mouth and the handle 88 is cut off, as with a scissors. In the alternative embodiment shown in FIGS. 6 and 7, the width and thickness of the handle 88 decrease adjacent the anterior portion 76 of the U-shaped base 62, thereby forming a tab 90 by which the handle 88 can be torn away from the U-shaped base 62.

The present invention also includes a sizing kit which may be generally seen in FIGS. 8 through 15. The sizing kit 139 generally comprises a bleaching tray sizing means 140 and a dentition impression plate 144 which will permit the receipt of a dentition imprint 156 for comparison of the impression plate 144 with the sizing chart 142 of the mouthguard sizing means 140.

Referring specifically to FIG. 8, the upper and lower dentitions 110 and 112 of a person are shown. The teeth of an individual or person include incisors 114, canine or eye teeth 116, bicuspids 118 and molars 120. The dentition 110 or 112 generally extends from one molar 120 side around the bicuspids 118, canines 116, incisors 114 and molars 120 of the other molar side generally shown as a C for circumference.

It is well known that a person's mouth, teeth and jaws vary considerably in size from children to large adults. Consequently it is imperative that the correct size (small to extra large) be selected for the appropriate bleaching tray 60 fitting to the wearer. After the appropriately sized bleaching tray 60 is selected, the sealing portion 61 generally may be softened by momentary placement in boiling water after which it is fit and vacuumed against the teeth and gums of the wearer.

Figure 9:
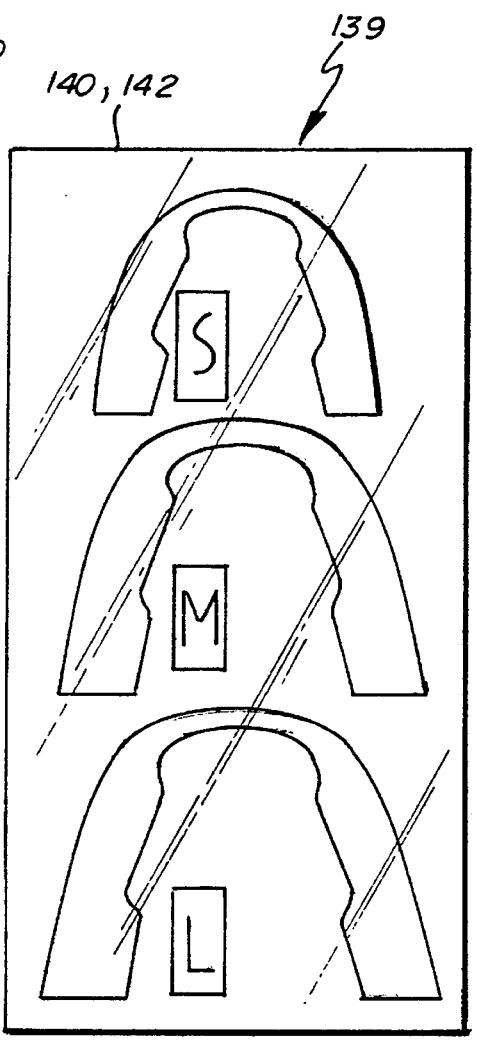
FIG. 9 is a near actual size top plan view of a dental tray sizing chart.
Figure 13:
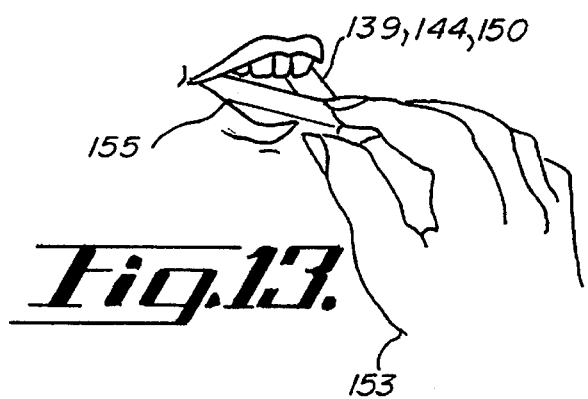
FIG. 13 is a perspective view of the V-shaped sizing strip being placed into a mouth for dentition impression upon the strip.
Figure 14:
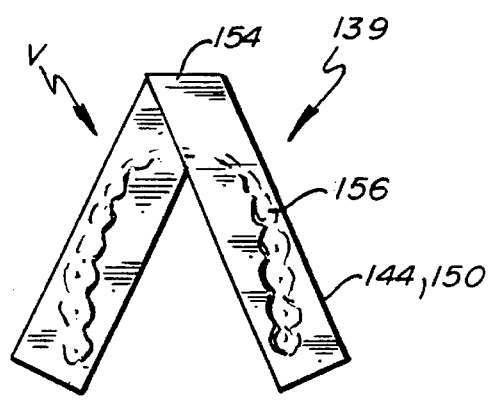
FIG. 14 is a top plan view of the V-shaped sizing strip bearing a dentition imprint.

Referring to FIG. 9, the bleaching tray sizing means 140 takes the form of a sizing chart 142. However, the sizing means 140 may simply be various sized bleaching trays 60. Bleaching trays 60 generally range from Small, Medium to Large. The sizing chart 142 is a simple and inexpensive way to show the actual true-to-life sizes of Small, Medium and Large bleaching trays 60. The chart 142 may be translucent for easy comparison of the impressions plate 144 placed therebelow as appreciated below.

Figure 10:
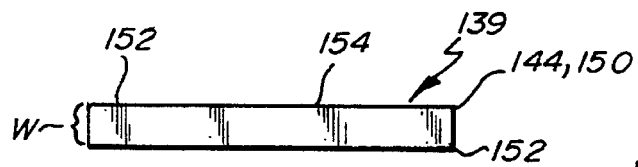
FIG. 10 is a top plan view of the elongate sizing strip.
Figure 11:
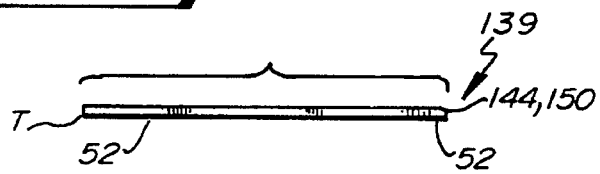
FIG. 11 is a side elevational view of the elongate sizing strip.
Figure 12:
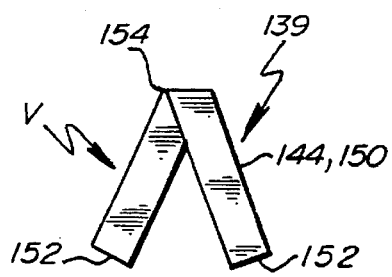
FIG. 12 is a top plan view of the elongate sizing strip folded to a V-shape.

Referring to FIGS. 10 through 12, the dentition impression plate 144 suitably may be seen. The plate may take any planar shape. In the preferred embodiment, the impression plate 144 takes the shape of an elongate sizing strip 150. The strip may be of a gum base together with calcium phosphate, flavoring, sodium saccharine and artificial coloring. Alternatively, the strip 150 may be made of a corn syrup based soft candy, such as a licorice, which may further include flour, sugar, corn starch and oil. The strip 150 may also be made of a wax base. The strip 150 may also take the form of nonedible materials capable of receiving impressions such as cardboard, tin foil, styrofoam and paper.

Again referring to FIGS. 10 through 12, the elongate sizing strip 150 has end portions 152 and an intermediate portion 154. The strip 150 generally has a length L equivalent to the circumference C or the complete extension of the dentition 110 as shown in FIG. 8. More specifically but only illustratively, the strip 50 may be approximately 6¼" (15 to 16 centimeters). The strip 150 also has a width W which should be at least as great as the largest molars 20 as shown in FIG. 8. More specifically but again illustratively, the width may generally be 7/16" (1.5 centimeters). To receive an impression, it is important that the sizing strip 150 suitably have some thickness T. Again, more specifically but only illustratively, a thickness T of 3/16" (0.4 centimeters) has been found to be suitable.

Referring to FIGS. 10 through 13, after the sizing strip is removed from packaging, it is generally folded into a V-shape at its intermediate portion 154. Thereafter, the user takes his or her hand 153 and places the V-shaped sizing strip 150 into the mouth 155 after which the lower jaw forces the sizing strip upwardly onto the upper dentition 110 to form a dentition imprint 156 clearly shown in FIG. 14 after the sizing strip 150 is removed from the user's mouth 155. Thereafter, the dentition imprint 156 on the sizing strip 150 is compared to the translucent or semi-transparent sizing chart 142 to assist the user in determining whether they should utilize a Small, Medium or Large bleaching tray. Alternatively, the sizing strip 150 may be compared to variously sized actual bleaching trays 60.

The present invention may be embodied in other specific forms without departing from the spirit or essential attributes thereof; therefore, the illustrated embodiment should be considered in all respects as illustrative and not restrictive, reference being made to the appended claims rather than to the foregoing description to indicate the scope of the invention.

I claim:

1. A composite bleaching tray for a user having an upper jaw with anterior teeth, posterior teeth with occlusal surfaces, and fossae with cartilage forming sockets, and a movable lower jaw with anterior teeth, posterior teeth with occlusal surfaces and condyles movably fitted within the sockets forming the temporomandibular joints, the bleaching tray comprising:

a) A U-shaped base made of a first material having an outer wall with an inner surface, bottom wall, anterior portion, and posterior portion;

b) a flexible and tough sealing portion made of a second material, injection molded to the top of said outer wall and to said bottom wall, forming an inner lingual wall for said U-shaped base;

c) a pair of posterior pads, each integral to said bottom wall of said posterior portion of said U-shaped base for creating a breathing airway and facilitating speech, and d) wherein the outer wall of the U-shaped base has a plurality of pockets on its inner surface facing the channel, for receiving bleaching gel.

2. The composite bleaching tray of claim 1, wherein the first material is a nonsoftening, resilient, low compression elastomer and wherein the sealing portion second material is a softenable thermoplastic.

3. The composite dental bleaching tray of claim 2, wherein the second material is made from a thermoplastic comprised of a copolymer of ethylene and vinyl acetate.

4. The composite dental bleaching tray of claim 2, wherein the first material is made from an elastomeric material selected from the group consisting of thermoplastic rubber and vulcanized rubber.

5. The composite dental bleaching tray of claim 1, further comprising a channel for receiving the teeth of the upper jaw, said channel being formed between the inner, lingual wall of the sealing portion and the outer wall and bottom wall of the U-shaped base.

6. The composite dental bleaching tray of claim 1, further comprising a handle for immersing the bleaching tray in boiling water.

7. The composite dental bleaching tray of claim 6, wherein the handle is connected to the anterior portion of the U-shaped base.

8. The composite dental bleaching tray of claim 7, wherein the handle and U-shaped base are molded of a single piece of the second material.

9. The composite dental bleaching tray of claim 8, wherein the width and thickness of the handle decrease adjacent the anterior portion of the U-shaped base, thereby forming a tab by which the handle may be detached from the U-shaped base.

* * * * *